(12) United States Patent
Swanson et al.

(10) Patent No.: US 11,147,967 B2
(45) Date of Patent: Oct. 19, 2021

(54) MODULATION OF ALDOSTERONE VIA ADRENAL GLAND STIMULATION

(71) Applicant: Boston Scientific Neuromodulation Corporation, Valencia, CA (US)

(72) Inventors: Lynne E Swanson, Edina, MN (US); Barbara Huibregtse, Westborough, MA (US); Bryan A. Clark, Forest Lake, MN (US); Dennis B. Werner, Big Lake, MN (US); Natalie A. Brill, Sherman Oaks, CA (US); Michael X. Govea, Castaic, CA (US); Umang Anand, Plymouth, MN (US); William C. Stoffregen, Lake Elmo, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 90 days.

(21) Appl. No.: 16/163,811

(22) Filed: Oct. 18, 2018

(65) Prior Publication Data
US 2019/0111253 A1    Apr. 18, 2019

Related U.S. Application Data

(60) Provisional application No. 62/574,079, filed on Oct. 18, 2017.

(51) Int. Cl.
*A61B 5/00*    (2006.01)
*G16H 40/63*    (2018.01)
(Continued)

(52) U.S. Cl.
CPC ......... *A61N 1/36007* (2013.01); *A61N 1/306* (2013.01); *A61N 1/3606* (2013.01);
(Continued)

(58) Field of Classification Search
CPC .. A61N 1/36007; A61N 1/3614; A61N 1/306; A61N 1/3606; A61N 1/36139;
(Continued)

(56) References Cited

U.S. PATENT DOCUMENTS 7,363,076 B2    4/2008  Yun et al.
2004/0220621 A1   11/2004  Zhou et al.
(Continued)

FOREIGN PATENT DOCUMENTS

WO    02/70039    9/2002

OTHER PUBLICATIONS

Blankstein, R., and Bakris, G. L. (2008). Renal hemodynamic changes in heart failure. Heart Failure Clin, 4:411-423.
(Continued)

*Primary Examiner* — Michael W Kahelin
*Assistant Examiner* — George E Banis
(74) *Attorney, Agent, or Firm* — Faegre Drinker Biddle & Reath LLP

(57) ABSTRACT

Various aspects of the present disclosure are directed toward apparatuses, systems, and methods for delivering therapy to an adrenal gland of a patient. The apparatuses, systems, and methods may include a plurality of stimulation elements arranged configured to deliver stimulation energy through at least one of the plurality of stimulation elements to modulate aldosterone levels within the patient.

18 Claims, 4 Drawing Sheets

(51) Int. Cl.
| | |
|---|---|
| A61B 5/11 | (2006.01) |
| A61B 5/0205 | (2006.01) |
| A61B 5/021 | (2006.01) |
| A61B 5/024 | (2006.01) |
| A61M 1/10 | (2006.01) |
| A61M 1/12 | (2006.01) |
| A61N 1/36 | (2006.01) |
| A61N 1/30 | (2006.01) |
| A61N 1/05 | (2006.01) |
| A61N 1/375 | (2006.01) |
| A61N 1/372 | (2006.01) |

(52) U.S. Cl.
CPC ....... *A61N 1/3614* (2017.08); *A61N 1/36139* (2013.01); *A61N 1/0507* (2013.01); *A61N 1/36031* (2017.08); *A61N 1/36171* (2013.01); *A61N 1/36175* (2013.01); *A61N 1/3756* (2013.01); *A61N 1/37205* (2013.01)

(58) Field of Classification Search
CPC .............. A61N 1/36031; A61N 1/0507; A61N 1/36171; A61N 1/36175; A61N 1/37205; A61N 1/3756
See application file for complete search history.

(56) References Cited

U.S. PATENT DOCUMENTS

| | | | |
|---|---|---|---|
| 2005/0021092 A1 | 1/2005 | Yun et al. | |
| 2005/0153885 A1 | 7/2005 | Yun et al. | |
| 2009/0024195 A1* | 1/2009 | Rezai ................... | A61N 1/0558 607/116 |
| 2010/0198308 A1* | 8/2010 | Zhou ................... | A61N 1/3601 607/62 |
| 2010/0305664 A1* | 12/2010 | Wingeier ........... | A61N 1/36007 607/62 |
| 2016/0213791 A1* | 7/2016 | Voelker .............. | A61B 10/0012 |
| 2016/0263376 A1* | 9/2016 | Yoo ..................... | A61N 1/36007 |
| 2017/0106185 A1* | 4/2017 | Orts ..................... | A61N 1/0573 |

OTHER PUBLICATIONS

Gilbert, K. C., and Brown, N. J. (2014). Aldosterone and inflammation. Curr Opin Endocrinol Diabetes Obes., Author manuscript, pp. 1-10.
Kong, Y. W., Baqar, S., Jerums, G., and Ekinci, E. I. (2016). Sodium and its role in cardiovascular disease—The debate continues. Frontiers in Endocrinology, 7:164, pp. 1-17.
Nussberger, J., and Bohlender, J. (2013). Optimal blockade of the renin-angiotensin-aldosterone system. Nat. Rev. Cardiol., 10:183-184.
Onuigbo, M. A. C., and Onuigbo, N. T. C. (2008). Worsening renal failure in older chronic kidney disease patients with renal artery stenosis concurrently on renin angiotensin aldosterone system blockade: A prospective 50-month Mayo-Health-System clinic analysis. Q J Med., 101:519-527.
Orlando, L. A., Belasco, E. J., Patel, U. D., and Matchar, D. B. (2011). The chronic kidney disease model: A general purpose model of disease progression and treatment. BMC Medical Informatics & Decision Making, 11:41, pp. 1-8.
Ruilope, L. M. (2008). Angiotensin receptor blockers: RAAS blockade and renoprotection. Current Medical Research Opinion, 24(5), pp. 1285-1293.
Tylicki, L., Lizakowski, S., and Rutkowski, B. (2012). Renin-angiotensin-aldosterone system blockade for nephroprotection: current evidence and future directions. J Nephrol. 25(06):900-910.
Yoshitake, I., et al. (2016). Renin-angiotensin system control for chronic kidney disease patients undergoing coronary surgery. Ann Thorac Cardiovasc Surg, 22:291-297.
Zhong, J., Yang, H., and Fogo, A. B. (2016). A perspective on chronic kidney disease progression. AJP Renal Physiology, 25 pp.

* cited by examiner

MODULATION OF ALDOSTERONE VIA ADRENAL GLAND STIMULATION

CROSS-REFERENCE TO RELATED APPLICATION

This application claims priority to Provisional Application No. 62/574,079, filed Oct. 18, 2017, which is herein incorporated by reference in its entirety.

TECHNICAL FIELD

The present disclosure relates to medical devices and methods for providing stimulation therapy. More specifically, the disclosure relates to devices and methods for delivering therapy to an adrenal gland of a patient.

BACKGROUND

Aldosterone levels in a patient are implicated as a major contributor to the progression of renal and heart diseases, and is also linked to fibrosis and inflammation, with patients having high aldosterone levels being more susceptible to premature vascular disease, cardiac fibrosis and vessel wall inflammation.

Renal and heart diseases are commonly treated with oral drug therapy. Electrical stimulation, however, may be therapeutic in a variety of diseases and disorders. Leads used in electrical stimulation may be implanted within, adjacent to, or near a targeted area. Leadless technologies (including nanotechnology) are also used in electrical stimulation. In certain instances, the lead or leads may be arranged near nerves, muscles, or other tissue to affect modulation of aldosterone levels within a patient.

SUMMARY

In Example 1, an apparatus for delivering therapy to an adrenal gland of a patient, the apparatus including: a housing configured to attach to a portion of the adrenal gland of the patient; and a plurality of stimulation elements arranged with the housing configured to deliver stimulation energy through at least one of the plurality of stimulation elements to modulate aldosterone levels within the patient.

In Example 2, the apparatus of Example 1, wherein the plurality of stimulation elements are configured to stimulate the adrenal gland and inhibit or block the release of aldosterone from the adrenal gland.

In Example 3, the apparatus of either of Examples 1 or 2, wherein the housing is a leadless body housing configured to engage the portion of the adrenal gland.

In Example 4, the apparatus of either of Examples 1 or 2, wherein the housing is a lead body configured to engage the portion of the adrenal gland.

In Example 5, the apparatus of any of Examples 1-4, wherein the plurality of stimulation elements are configured to deliver at least one of electrical stimulation, light stimulation, sound stimulation, thermal stimulation, and magnetic stimulation to the adrenal gland to modulate aldosterone levels within the patient.

In Example 6, the apparatus of any of Examples 1-5, wherein the plurality of stimulation elements are configured to deliver stimulation to maintain aldosterone levels within the patient within normal basal levels.

In Example 7, the apparatus of Example 6, further comprising a sensor configured to measure the aldosterone levels within the patient and alter the stimulation energy delivered through the at least one of the plurality of stimulation elements to maintain the aldosterone levels within the patient within the normal basal levels of the patient.

In Example 8, the apparatus of Example 7, wherein the sensor is arranged with the housing.

In Example 9, the apparatus of Example 7, wherein the housing comprises a communications component configured to communicate wireless signals, and the sensor is configured to measure the aldosterone levels within the patient and communicate feedback to the communications component via wireless signals to alter the stimulation energy delivered through the at least one of the plurality of stimulation elements to maintain the aldosterone levels within the patient within the normal basal levels of the patient.

In Example 10, the apparatus of any of Examples 8-9, wherein the sensor is at least one of a chemical sensor configured to sense chemical levels within the patient associated with the aldosterone levels, a blood pressure sensor configured to sense blood pressure levels associated with the aldosterone levels, a time of day sensor configured to sense blood pressure levels associated with the aldosterone levels, and a sleep status sensor configured to sense blood pressure levels associated with the aldosterone levels.

In Example 11, the apparatus of any of Examples 1-10, wherein the plurality of stimulation elements are configured to delivery stimulation energy on a duty cycle based on a metabolization time of aldosterone within the patient.

In Example 12, the apparatus of any of Examples 1-11, wherein the plurality of stimulation elements are configured to delivery stimulation energy to a cortex or outer layer of the adrenal gland of the patient.

In Example 13, the apparatus of Example 12, wherein the delivery of stimulation energy modulates the renin-angiotensin-aldosterone system (RAAS) within the patient.

In Example 14, the apparatus of Example 13, wherein the delivery of stimulation energy interrupts the renin-angiotensin-aldosterone system (RAAS), thereby lowering production of aldosterone by the patient.

In Example 15, the apparatus of any of Examples 1-14, wherein the delivery of stimulation energy lessens aldosterone levels in the patient to treat at least one of heart failure, chronic kidney disease, and cardiorenal syndrome.

In Example 16, an apparatus for delivering therapy to an adrenal gland of a patient, the apparatus including: a housing configured to attach to a portion of the adrenal gland of the patient; and a plurality of stimulation elements arranged with the housing configured to deliver stimulation energy through at least one of the plurality of stimulation elements to modulate production of aldosterone by the patient.

In Example 17, the apparatus of Example 16, wherein the plurality of stimulation elements are configured to stimulate the adrenal gland and inhibit or block the release of aldosterone by the patient.

In Example 18, the apparatus of Example 16, wherein the housing is a leadless housing configured to engage the portion of the adrenal gland.

In Example 19, the apparatus of Example 16, wherein the housing is a lead body configured to engage the portion of the adrenal gland.

In Example 20, the apparatus of Example 16, wherein the plurality of stimulation elements are configured to deliver at least one of electrical stimulation, light stimulation, sound stimulation, thermal stimulation, and magnetic stimulation to the adrenal gland to modulate aldosterone levels within the patient.

In Example 21, the apparatus of Example 16, wherein the plurality of stimulation elements are configured to deliver stimulation to maintain aldosterone levels within the patient within normal basal levels.

In Example 22, the apparatus of Example 16, wherein the plurality of stimulation elements are configured to delivery stimulation energy on a duty cycle based on a metabolization time of aldosterone within the patient.

In Example 23, the apparatus of Example 16, wherein the plurality of stimulation elements are configured to delivery stimulation energy at a frequency between 2 Hz and 20 kHz.

In Example 24, the apparatus of Example 16, wherein the plurality of stimulation elements are configured to delivery stimulation energy to a cortex or outer layer of the adrenal gland of the patient.

In Example 25, the apparatus of Example 24, wherein the delivery of stimulation energy modulates the renin-angiotensin-aldosterone system (RAAS) within the patient.

In Example 26, the apparatus of Example 25, wherein the delivery of stimulation energy interrupts the renin-angiotensin-aldosterone system (RAAS) thereby lowering production of aldosterone by the patient.

In Example 27, the apparatus of Example 16, wherein the delivery of stimulation energy lessens aldosterone plasma levels in the patient to treat at least one of heart failure, chronic kidney disease, and cardiorenal syndrome.

In Example 28, an apparatus for delivering therapy to an adrenal gland of a patient, the apparatus including: a housing configured to attach to a portion of the adrenal gland of the patient; a plurality of stimulation elements arranged with the housing configured to deliver stimulation energy through at least one of the plurality of stimulation elements to modulate aldosterone levels within the patient; and a sensor configured to measure the aldosterone levels within the patient and alter the stimulation energy delivered through the at least one of the plurality of stimulation elements.

In Example 29, the apparatus of Example 28, wherein the sensor is configured to alter the stimulation energy delivered through the at least one of the plurality of stimulation elements to maintain the aldosterone levels within the patient within normal basal levels.

In Example 30, the apparatus of Example 28, wherein the sensor is arranged with the housing.

In Example 31, the apparatus of Example 28, wherein the housing comprises a communications component configured to communicate wireless signals, and the sensor is configured to measure the aldosterone levels within the patient and communicate feedback to the communication component via wireless signals to alter the stimulation energy delivered through the at least one of the plurality of stimulation elements to maintain the aldosterone levels within the patient within the normal basal levels of the patient.

In Example 32, the apparatus of Example 28, wherein the sensor is at least one of a chemical sensor configured to sense chemical levels within the patient associated with the aldosterone levels, a blood pressure sensor configured to sense blood pressure levels associated with the aldosterone levels, a time of day sensor configured to sense blood pressure levels associated with the aldosterone levels, and a sleep status sensor configured to sense blood pressure levels associated with the aldosterone levels.

In Example 33, a method of delivering therapy to an adrenal gland of a patient, the method including: delivering a housing to a portion of the adrenal gland of the patient, the housing including a plurality of stimulation elements arranged with the housing; and delivering stimulation energy through at least one of a plurality of electrodes leadless implantable medical to modulate aldosterone levels within the patient.

In Example 34, the method of Example 33, wherein delivering the stimulation energy includes delivering stimulation energy on a duty cycle based on a metabolization time of aldosterone within the patient In Example 35, the method of Example 33, further comprising using a sensor to measure the aldosterone levels within the patient and altering the stimulation energy delivered through the at least one of the plurality of stimulation elements based on measured aldosterone levels.

While multiple embodiments are disclosed, still other embodiments of the present disclosure will become apparent to those skilled in the art from the following detailed description, which shows and describes illustrative embodiments of the subject matter disclosed herein. Accordingly, the drawings and detailed description are to be regarded as illustrative in nature and not restrictive.

Figure 1:
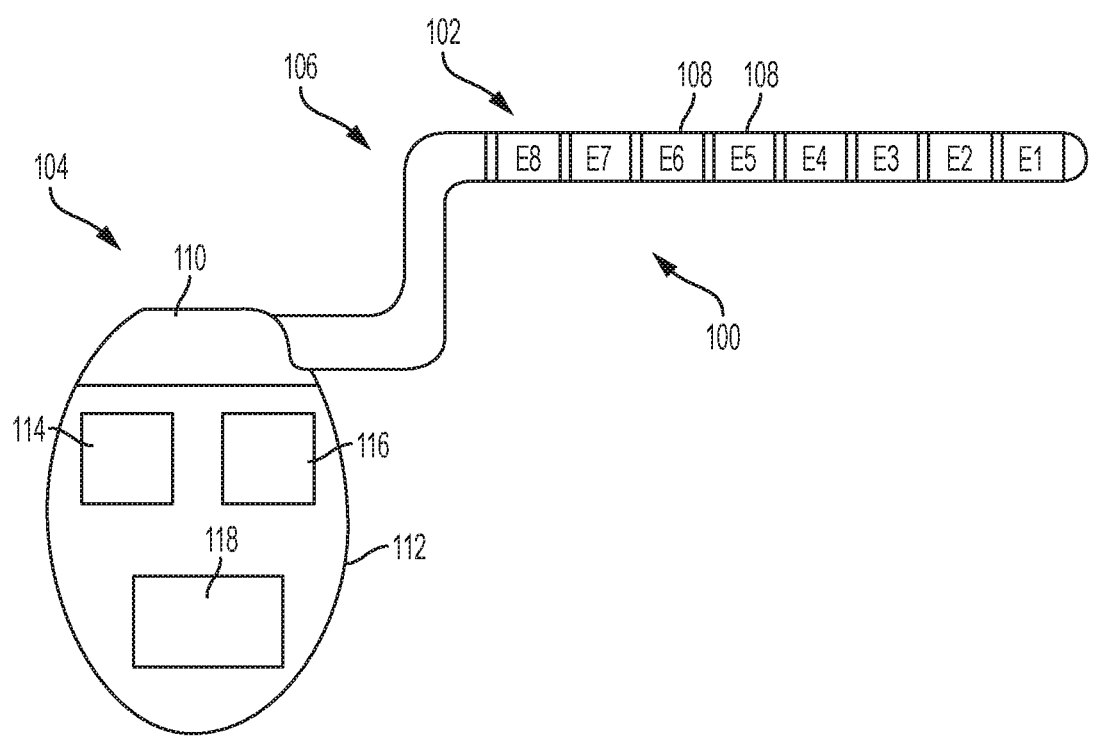
FIG. 1 is an example illustration of an adrenal gland therapy system, in accordance with embodiments of the disclosure

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements or settings (or ranges of measurements or settings), "about" and "approximately" may be used, interchangeably, to refer to a measurement or setting that includes the stated measurement or setting and that also includes any measurements or settings that are reasonably close to the stated measurement or setting, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements or settings, adjustments made to optimize performance and/or structural parameters in view of differences in measurements or settings associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Various aspects of the present disclosure relate to apparatuses, methods, and systems method directed toward systemic modulation of aldosterone from an adrenal gland or glands of a patient. High levels of aldosterone may occur in heart failure, cardio-renal syndrome, chronic kidney disease, post-myocardial infarction care or other hyperaldosteronism conditions such as Conn's syndrome, Cushings disease, or other ailments affecting the heart of the renal system such as hypertension (refractory or otherwise) and metabolic syndromes. Various aspects of the present disclosure relate to downregulation of aldosterone in such disease states. Low levels of aldosterone occur in disease states such as within sufficient hormone levels such as Addison's disease, congenital adrenal hyperplasia, diseases of the pituitary or hypothalamus or diabetic nephropathy. Various aspects of the present disclosure relate to upregulation of aldosterone in such disease states. A patients' renin-angiotensin-aldosterone-system (RAAS) may be modulated due to chemical or other systemic levels of a patient. For example, the RAAS may be activated by low sodium, hypotension or sympathetic activation, resulting in renin release from the kidney, with a subsequent cascade of Angiotensin I released from the lungs, then Angiotensin II from the liver. Angiotensin II in turn activates aldosterone from the adrenal glands. Stimulation of the adrenal gland or adrenal glands of the patient by a medical device may avoid pharmaceutical therapy, which may have side effects and compliance issues. In addition, a subset of patients who may not tolerate medications or have the option for pharmaceutical drug intervention.

The adrenal glands, specifically the cortex of the adrenal glands, may be stimulated to inhibit or alter aldosterone production. Aldosterone is produced predominantly by the adrenal glands and but also produced in minimal amounts by other extra-renal sites (e.g., within the heart and blood vessels). Transmural stimulation of the adrenal gland demonstrates a rapid non-hemodynamic blocking or blunting/inhibitory effect of aldosterone production or may alternatively increase aldosterone production as noted above.

FIG. 1 is an example illustration of an adrenal gland therapy system 100, which includes an adrenal gland therapy lead 102 and a controller 104 in accordance with embodiments of the disclosure. The lead 102 may include an elongated cylindrical lead body 106. The lead 102 includes a number of stimulation elements 108 arranged on the lead body 106. The stimulation elements 108 (e.g., electrodes) may be arranged circumferentially around the lead 102, for example, as ring electrodes mounted around the lead body 106. In embodiments, the stimulation elements 108 may extend at least approximately around the circumference of the lead body 106. In embodiments, one or more of the stimulation elements 108 may extend partially around the circumference of the lead body 106. In some instances, for example, the plurality of stimulation elements 108 may be segmented electrodes that are circumferentially and axially disposed about the lead body 106. Each of the plurality of illustrated stimulation elements 108 are labeled E1-E8, however the actual number and shape of leads and electrodes vary according to the application.

As shown, the adrenal gland therapy lead 102 is operatively coupled to the controller 104. A connector 110 arranged with the controller 104 couples an end of the adrenal gland therapy lead 102 to the controller 104, thereby operatively (e.g., communicatively, electrically, and/or physically) coupling the stimulation elements 108 to the internal electronics within the controller 104. In embodiments, the controller 104 may be configured to communicate wirelessly with one or more leads 102, in which case, the controller 104 may include one or more wireless communication antennas, coils, and/or the like. The controller 104 may also include a housing 112, which houses electronic and other components. In embodiments, the controller 104 may include a pulse generator that may be implantable within a patient (e.g., an implantable pulse generator (IPG)), or may be configured to be positioned external to the patient. In instances where the controller 104 is implantable, the housing 112 may be formed of an electrically conductive, biocompatible material, such as titanium, and may form a hermetically sealed compartment configured to protect the internal electronics from the housing tissue and fluids.

The housing 112 may enclose sensing circuitry 114 configured to communicate with a sensor 118 arranged with the housing 112 or on the lead 102. The sensor 118 is configured to measure the aldosterone levels within the patient (e.g., within plasma of the patient). In addition, the sensor 118 may communicate with the sensing circuitry 114 to alter the stimulation energy delivered through one or more of the stimulation elements 108 based on the sensed aldosterone levels within the patient. The housing 112 may also enclose pulse generation circuitry 116 that delivers stimulation energy via one or more of the stimulation elements 108. According to various embodiments, the sensing circuitry 114 (or aspects thereof) and/or the pulse generation circuitry 116 (or aspects thereof) may be configured to be implanted in the patient and/or disposed external to the patient. That is, for example, in embodiments, the sensing circuitry 114 and the pulse generation circuitry 116 may be integrated within a processor disposed in an implantable medical device (e.g., the controller 104) and/or an external medical device. The sensing circuitry 114 (or aspects thereof) and/or the pulse generation circuitry 116 (or aspects thereof) may be implemented in any combination of hardware, firmware, and software. For example, the sensing circuitry 114 may be, or include, a first algorithm, virtual processor, and/or process implemented by a processor, and, similarly, the pulse generation circuitry 116 circuit may be, or include, a second algorithm, virtual processor, and/or process implemented by a processor. In embodiments, the sensing circuitry 114 may be, or include, a first set of physical and/or virtual circuit elements, and, similarly, the pulse generation circuitry 116 may be, or include, a second set of physical and/or virtual circuit elements.

In certain instances, the controller 104 may include a programmable micro-controller or microprocessor, and may include one or more programmable logic devices (PLDs) or application specific integrated circuits (ASICs). In some implementations, the controller 104 may include memory as well. Although embodiments of the present system 100 are described in conjunction with a controller 104 having a microprocessor-based architecture, it will be understood that the controller 104 (or other device) may be implemented in any logic-based integrated circuit architecture, if desired. The controller 104 may include digital-to-analog (D/A) converters, analog-to-digital (ND) converters, timers, counters, filters, switches, and/or the like.

The sensing circuitry 114 may be configured to receive a data from the sensor 118, and analyze the data to determine aldosterone levels within the patient. The sensor 118 may be, for example, a chemical sensor configured to sense chemical levels within the patient associated with the aldosterone levels (e.g., potassium or sodium), a blood pressure sensor configured to sense blood pressure levels associated with the aldosterone levels, a time of day sensor configured to sense blood pressure levels associated with the aldosterone levels, or a sleep status sensor configured to sense blood pressure levels associated with the aldosterone levels as discussed in further detail below with reference to FIGS. 3-4.

The stimulation energy may be in the form of a pulsed electrical waveform provided to one or more of the stimulation elements 108 in accordance with a set of stimulation parameters, which may be programmed into the controller 104, transmitted to the controller 104, and/or the like. Stimulation parameters may include, for example, electrode combinations that define the electrodes that are activated as anodes (positive), cathodes (negative), turned on, turned off (zero), percentage of stimulation energy assigned to each electrode (fractionalized electrode configurations), and/or electrical pulse parameters, which define the pulse amplitude (e.g., measured in milliamps or volts depending on whether the controller 104 supplies constant current or constant voltage to one or more of the stimulation elements 108), pulse duration (e.g., measured in microseconds), pulse rate (e.g., measured in pulses per second), pulse waveform, and/or burst rate (e.g., measured as the stimulation on duration X and stimulation off duration Y). The pulse generation circuitry 116 may be capable of delivering the stimulation energy to the one or more of the stimulation elements 108 over multiple channels or over only a single channel.

Stimulation energy may be transmitted to the tissue in a monopolar (or unipolar) or multipolar (e.g., bipolar, tripolar, etc.) fashion. Monopolar stimulation occurs when a selected one or more of the stimulation elements 108 is activated and transmits stimulation energy to tissue. Bipolar stimulation, a type of multipolar stimulation, occurs when two of the stimulation elements 108 are activated as an anode and cathode, so that stimulation energy is transmitted between the stimulation elements 108. Multipolar stimulation also may occur when more than two (e.g., three, four, etc.) of the stimulation elements 108 are activated, e.g., two as anodes and a third as a cathode, or two as cathodes and a third as an anode. In certain instances, the pulse generation circuitry 116 may individually control the magnitude of electrical current flowing through each of the electrodes. In these instances, current generators may be used to supply current-regulated amplitudes to selectively generate independent current sources for one or more of the stimulation elements 108.

Figure 2:
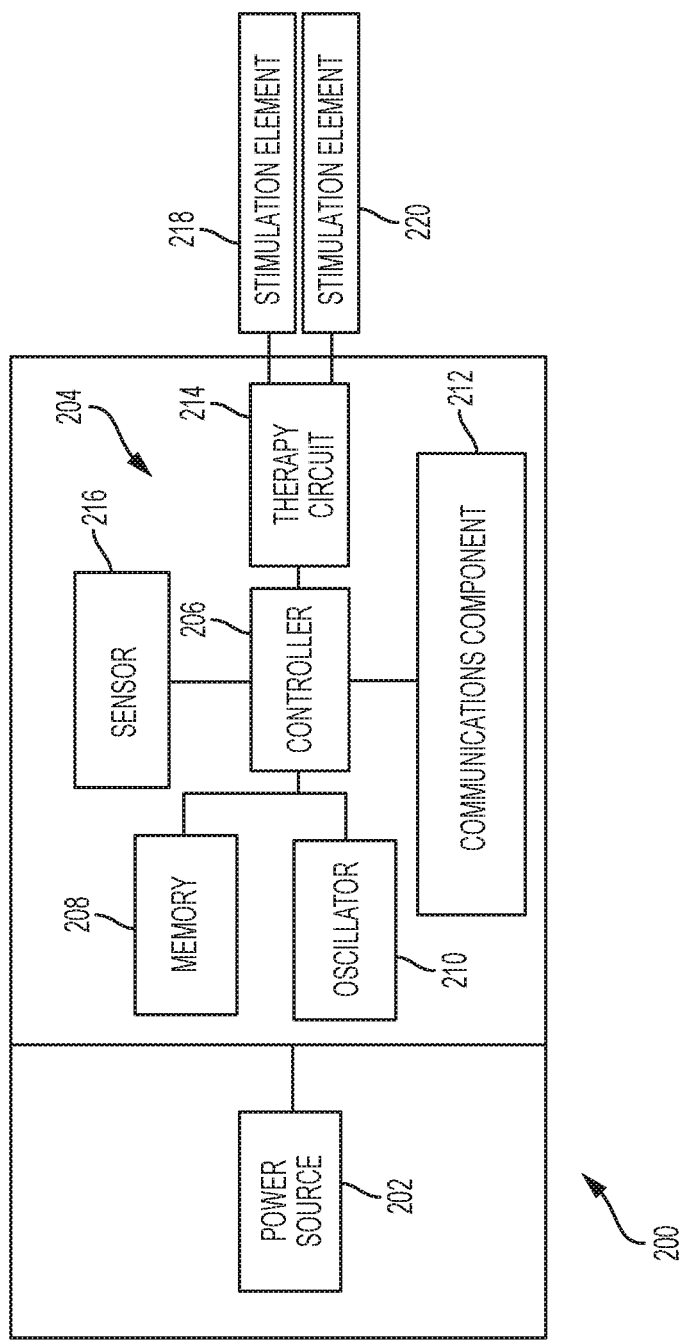
FIG. 2 is a schematic block diagram of a leadless implantable medical device, in accordance with aspects of embodiments of the disclosure.
Figure 3:
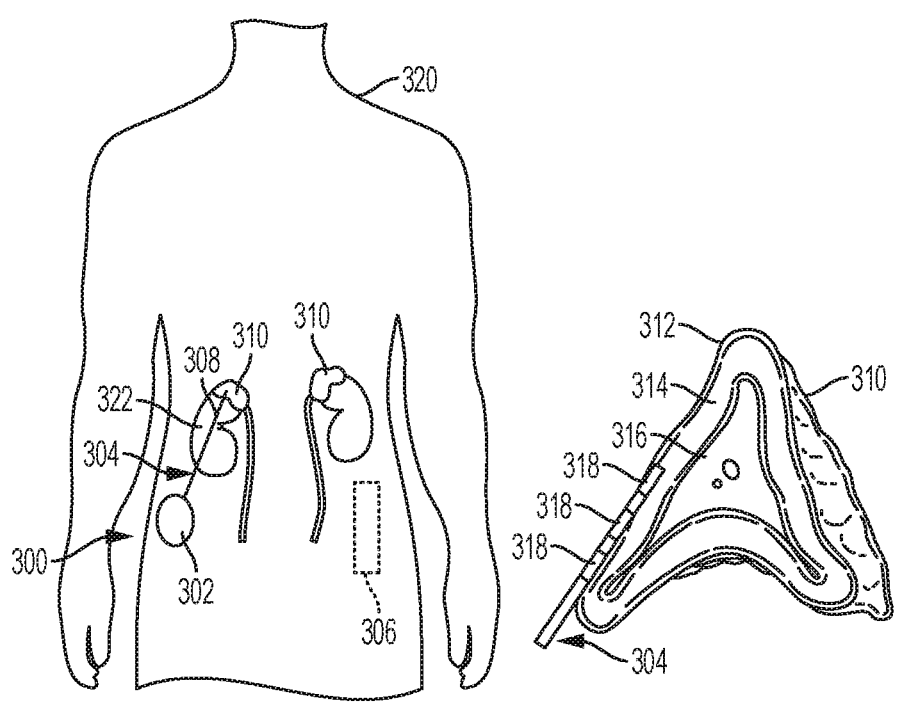
FIG. 3 is an example illustration of an adrenal gland therapy system in accordance with embodiments of the disclosure.

FIG. 2 is a schematic block diagram of a leadless implantable medical device 200, in accordance with aspects of embodiments of the disclosure. As shown in FIG. 2, the leadless implantable medical device 200 includes a power source 202 that powers operational circuitry 204 of the leadless implantable medical device 200. The operational circuitry 204 includes a controller 206 coupled to a memory 208. An oscillator 210 coupled to the controller 206 may be used as a clocking mechanism to provide timing functions to the controller 206. In certain instances, other types of clocking mechanisms may be used as well as, or in addition, to the oscillator 210. The operational circuitry 204 also includes a communications component 212, a therapy circuit 314, and a physiological sensor 316. As shown in FIG. 3, the therapy circuit 314 is coupled to stimulation elements 218 and 220 and is configured to provide stimulation energy to the stimulation elements 218 and 220, which, in turn, provide the energy to a patient's adrenal gland. The IMD 200 may include more than two stimulation elements 218 and 220. Additionally, the communications component 212 may include a transceiver and an antenna.

The IMD 200 may also include a sensor 216 configured to sense and analyze aldosterone levels within the patient. The sensor 216 may be, for example, a chemical sensor configured to sense chemical levels within the patient associated with the aldosterone levels, a blood pressure sensor configured to sense blood pressure levels (e.g., associated with sodium or potassium levels of a patient or a blood pressure surrogates such as S2 heart sounds or pulse transit times) associated with the aldosterone levels, a time of day sensor (as associated with the aldosterone levels), or a sleep status sensor (as associated with the aldosterone levels) as discussed in further detail below with reference to FIGS. 3-4.

FIG. 3 is an example illustration of an adrenal gland therapy system 300 in accordance with embodiments of the disclosure. The adrenal gland therapy system 300 includes a controller 302 (e.g., a pulse generator) that houses electronic and other components, a lead 304 configured to attach to a portion of an adrenal gland 310 of the patient 320. The lead 304 is coupled to the controller 302, and optionally a sensor 306. The lead 304 may include a lead body 308.

FIG. 3 also includes an inset portion highlighting the anatomy of the adrenal gland 310, which is located above the kidney 322. A capsule 312 surrounds the adrenal gland 310. The lead body 308 may be attached to an exterior surface of the capsule 312, within the capsule 312, and/or to an interior surface of the capsule 312 (e.g., between the capsule and the remaining portions of the adrenal gland 310). The adrenal gland 310 also includes a cortex 314 which produces steroid hormones, and a medulla 316.

The lead body 308 may include a plurality of stimulation elements 318 arranged with the lead body 308. The stimulation elements 318 are configured to deliver stimulation energy (through at least one of the plurality of stimulation elements) to modulate production of aldosterone by the patient. In certain instances, the controller 302, physically connected to the lead body 308 and electronically coupled to the plurality of stimulation elements 318, may be configured to instruct delivery of the stimulation energy through one or more of the plurality of stimulation elements 318 to modulate stimulate the adrenal gland to inhibit or block the release of aldosterone by the patient 320. Aldosterone is not stored at the site of synthesis within the adrenal gland 310, but controlled by the rate of synthesis as the housing of the patient 320 regulates salt and water balance, within the cortex 314 of the adrenal gland 322. The cortex 314 is full of lipids rich in esterified cholesterol, hydrolyzed by pancreatic enzymes to create cholesterol, from which all the enzymatic reactions occur to create aldosterone.

In certain instances, the delivery of stimulation energy by the stimulation elements 318 modulates the renin-angiotensin-aldosterone-system (RAAS) of the patient 320. In certain instances, stimulation may indirectly interrupt the RAAS, for example, by interrupting the biosynthesis pathway within the cortex 314, changing the signaling cascades within the cortex 314, a non-genomic type of response, or other neural modulation. Aldosterone may be stimulated by Angiotensin II (part of the RAAS). Low sodium in the blood or low arterial blood pressure (typically detected in the kidney), may stimulate the lungs to release Angiotensin I, which in turn stimulates the liver to produce Angiotensin II, which acts on receptors in the adrenal gland 310 producing a rise in aldosterone. Lower levels of potassium may also act as a stimulus for aldosterone production. In addition, neural pathways may also control aldosterone modulation. Stimulation may also indirectly affect Angiotensin II via neural modulation, via aspects of the biosynthesis pathway, or via signaling cascades. As noted above, aldosterone is implicated as the major contributor to the progression of renal disease and heart failure, and is heavily linked to fibrosis and inflammation. Patients with high aldosterone levels may be more susceptible to premature vascular disease, cardiac fibrosis and vessel wall inflammation. The delivery of stimulation energy by the stimulation elements 318 may interrupt the RAAS by lowering production of aldosterone by the patient 320.

In certain instances, the plurality of stimulation elements 318 are configured to delivery stimulation energy to the cortex 314 of the patient 320. In the cortex 314, the cells that synthesize aldosterone respond based on hemodynamics of the patient 320 and electrolyte imbalances in the bloodstream. In addition, the splanchnic nerve of the patient 320 travels through the cortex 314 and terminates in the medulla 316. Stimulation of the cortex 314 by the stimulation elements 318 may influence aldosterone production by stimulating the splanchnic nerve. In addition, the cortex 314 may be sensitive to stimulation, such that stimulation by the stimulation elements 318 may blunt, block or otherwise influence the RAAS, independent of the sympathetic nervous system.

In certain instances, the plurality of stimulation elements 318 are configured to deliver electrical stimulation, light stimulation, sound stimulation, thermal stimulation, and/or magnetic stimulation to the adrenal gland 310 to modulate aldosterone levels within the patient 320. As noted above, the controller 302, to which the stimulation elements 318 are coupled, may include circuitry (e.g., as described with reference to FIG. 1) that instructs delivery of the stimulation energy. The controller 302 and the stimulation elements 318 may be specifically configured to deliver the intended type of stimulation energy. For example, the stimulation elements 318 include electrodes, and the controller 302 includes pulse generation circuitry, when the stimulation elements 318 and the controller 302 are configured to delivery configured to deliver electrical stimulation energy. In addition, the stimulation elements 318 include light emitting diodes (LEDs), and the controller 302 includes pulse generation circuitry, when the stimulation elements 318 and the controller 302 are configured to delivery configured to deliver light stimulation energy. Further, the stimulation elements 318 may include sound emitting structures or acoustic elements to deliver sound stimulation, thermocouples to deliver thermal stimulation, and/or magnetic structures to deliver magnetic stimulation.

The plurality of stimulation elements 318 may be configured to deliver stimulation to maintain aldosterone levels within the patient within normal basal levels of the patient. In certain instances, the controller 302 may be configured to intermittently or continuously instruct delivery of the stimulation energy through different combinations of the one or more of the stimulation elements 318. In addition, the controller 302 may include circuitry (e.g., as described with reference to FIG. 1) that instructs delivery of the stimulation energy through one or more of the stimulation elements 318 on a duty cycle based on a metabolization time of aldosterone. The duty cycle may include applying stimulation for approximately 25% of a time period (e.g., seconds, minutes, hours, or days), and withhold stimulation for approximately 75% the time period (e.g., minutes, hours, or days). The duty cycle control of delivery of the stimulation energy may reduce battery consumption of the controller 302. In addition, the stimulation energy may be delivered at a frequency between approximately 2 Hz and approximately 20 kHz or between approximately 20 Hz and approximately 4000 Hz. The stimulation energy may be applied as bursts of energy including pulses at a frequency between approximately 2 Hz and approximately 20 kHz or between approximately 20 Hz and approximately 4000 Hz, or continuously. In addition, the frequency and/or pulse width stimulation and/or current energy may also be altered continuously or periodically altered over time.

The delivery of stimulation energy may lessen aldosterone levels in the patient to treat a number of diseases. As noted above, high aldosterone levels are associated with heart failure, chronic kidney disease, and cardiorenal syndrome. High aldosterone levels may further progression of these disease states, and may cause inflammation and fibrosis in the heart or kidneys 322 organs. In addition, high aldosterone levels may assist in treatment of hypertension as lowering of aldosterone levels may also lower blood pressure of the patient 320. Further lowering of aldosterone levels may also assist in treatment of bilateral tumors of the adrenal gland or Conn's Syndrome (primary hyperaldosteronism). Thus, by delivering stimulation energy via the stimulation elements 318, the aldosterone levels of the patient 320 may be lowered. In addition, the delivery of stimulation energy via the stimulation elements 318 may also upregulate release or increase production of aldosterone. Thus, increasing production of aldosterone through stimulation may assist in treatment of disease states with insufficient aldosterone levels such as Addison's disease, congenital adrenal hyperplasia, diseases of the pituitary or hypothalamus, and/or diabetic nephropathy.

The stimulation energy delivered may be altered in response to feedback based on the physical symptoms of the patient 320. Additionally, the controller 302 may instruct alteration of the stimulation energy provided to one or more of the plurality of stimulation elements 318 based on patient feedback. Therapy may be customized by calibrating to a target level or within normal basal levels of the patient based on a change in physical symptoms or based on data obtained by the sensor 306 and/or based on patient 320 or physician input on an external device, communicatively coupled with the controller 302, that may control the stimulation energy level. The aldosterone levels of the patient 320 may be sensed by the sensor 306 and provided as feedback to the controller 302, which may alter the stimulation energy to achieve desired aldosterone levels of the patient 320. The sensor 306, in connection with the controller 302, may be configured to alter the stimulation energy delivered through one or more of the plurality of stimulation elements 308 to maintain the aldosterone levels within the patient within normal basal levels of the patient or desired treatment zone. As shown in FIG. 3, the sensor 306 is arranged with the housing. In other instances, the sensor 306 may be incorporated with the controller 302 or with the lead body 308.

In addition to be being communicatively (and, in embodiments, physically) coupled to the lead body 308, the controller 302 may be communicatively coupled to the sensor 306. The controller 302 may be configured to receive a signal from the sensor 306 having data indicative of the aldosterone levels of the patient 320. Communication between the controller 302 and the sensor 306 may be, or include, a wireless communication link such as, for example, a short-range radio link, such as Bluetooth, IEEE 802.11, a proprietary wireless protocol, and/or the like (as is described in further detail with reference to FIG. 2). The controller 302 may also analyze the signal from the sensor 306 to calculate alteration of the stimulation energy, and communicate with the lead body 308 to alter the stimulation energy based on analysis of the signal.

The data indicative of the aldosterone levels of the patient 320 may be measured by the sensor 306, which may be a chemical sensor configured to sense chemical levels within the patient 320 associated with the aldosterone levels, a blood pressure sensor configured to sense blood pressure levels associated with the aldosterone levels, a time of day sensor, a sleep status sensor, or surrogate sensors such as sensors that sense heart (e.g, S2) sounds.

When the sensor 306 is a chemical sensor, the sensor 306 may be configured to sense chemical levels within the patient associated with the aldosterone levels such as sodium and/or potassium because, as noted above, aldosterone regulates both sodium and potassium. Because aldosterone lives within the RAAS, chemosensors monitoring renin, Angiotensin I, or Angiotensin II may also be utilized. Renin is an enzyme that leads to a series of chemical reactions resulting in the production of Angiotensin II, which in turn stimulate aldosterone release. If the patient 320 has high renin, Angiotensin I, Angiotensin II, sodium, and/or potassium as measured by the sensor 306, stimulation applied through the stimulation elements 318 downregulates Aldosterone production. If the patient 320 has low renin, Angiotensin I, Angiotensin II, sodium, and/or potassium as measured by the sensor 306, stimulation applied through the stimulation elements 318 up-regulates Aldosterone production. A reactive Oxygen Species (ROS) and/or inflammatory cytokine chemosensor may also be used as the sensor 306. If the patient 320 has high ROS or inflammatory cytokines, stimulation applied through the stimulation elements 318 downregulates Aldosterone production. If the patient 320 has low ROS or inflammatory cytokines, stimulation applied through the stimulation elements 318 up-regulates Aldosterone production.

The sensor 306 may also be a blood pressure sensor. Aldosterone plays a role in blood pressure regulation primarily through acting on organs such as the kidney 322 and colon to increase the amount of sodium reabsorbed into the blood stream (e.g., from sweat, urine, and the gut) and the amount of potassium removed through urine. Aldosterone also causes water to be reabsorbed along with sodium, increasing blood volume and blood pressure. If the patient 320 has high blood pressure, stimulation through the stimulation elements 318 applied to the adrenal gland downregulates aldosterone production. If the patient 320 has low blood pressure, stimulation through the stimulation elements 318 applied to the adrenal gland up-regulates aldosterone production. Thus, in order for the sensor 306 to provide feedback to the controller 306 to instruct and/or alter stimulation through the stimulation elements 318, the sensor 306, acting as a blood pressure sensor 306, may measure direct systolic, diastolic and/or mean blood pressure (BP) measure, or surrogates of blood pressure (e.g., S2 heart sound sphygmomanometer photoplethysmography (PPG) to measure pulse transit time, pulse amplitude, normalized pulse volume, or other parameters correlating with blood pressure). In certain instances, the sensor 306 may be located outside the patient 320 and may communicate with the controller 302. The sensor 306, for example, may be a blood pressure cuff.

A time of day and/or sleep status may also be used as the sensor 306. A desired aldosterone level of a healthy patient 320 is associated with a circadian rhythm. Thus, stimulation through the stimulation elements 318 may be applied to up or down regulate aldosterone levels of the patient 320 based on sensing whether the patient 320 is asleep or awake or based on the time of day. In addition, an activity sensor may be used as the sensor 306. Stimulation through the stimulation elements 318 may be applied to up or down regulate aldosterone levels of the patient 320 based on sensing whether the patient 320 is active.

The coordinated stimulation provided by the controller 302 may provide a closed-loop system which uses markers of aldosterone levels to optimize therapy. In certain instances, the sensor 306 may provide data to the controller 302 to enable predictive power to provide therapy only when needed or otherwise enabling improved therapy titration (e.g. stimulation amplitude, charge) and optimize clinical outcomes. The measurements of the sensor 306 may be collected by the controller 302 and aggregated to alter delivery of the stimulation energy provided through the plurality of stimulation elements 318. In certain instances, more than the system 300 may include multiple ones of the sensors 306 described above that may coordinate measurement and effective regulation of aldosterone levels in the patient 320.

The illustrative components shown in FIG. 3 are not intended to suggest any limitation as to the scope of use or functionality of embodiments of the disclosed subject matter. Neither should the illustrative components be interpreted as having any dependency nor requirement related to any single component or combination of components illustrated therein. Additionally, any one or more of the components depicted in any of the FIGS. 1-4 may be, in embodiments, integrated with various other components depicted therein (and/or components not illustrated), all of which are considered to be within the ambit of the disclosed subject matter.

Figure 4:
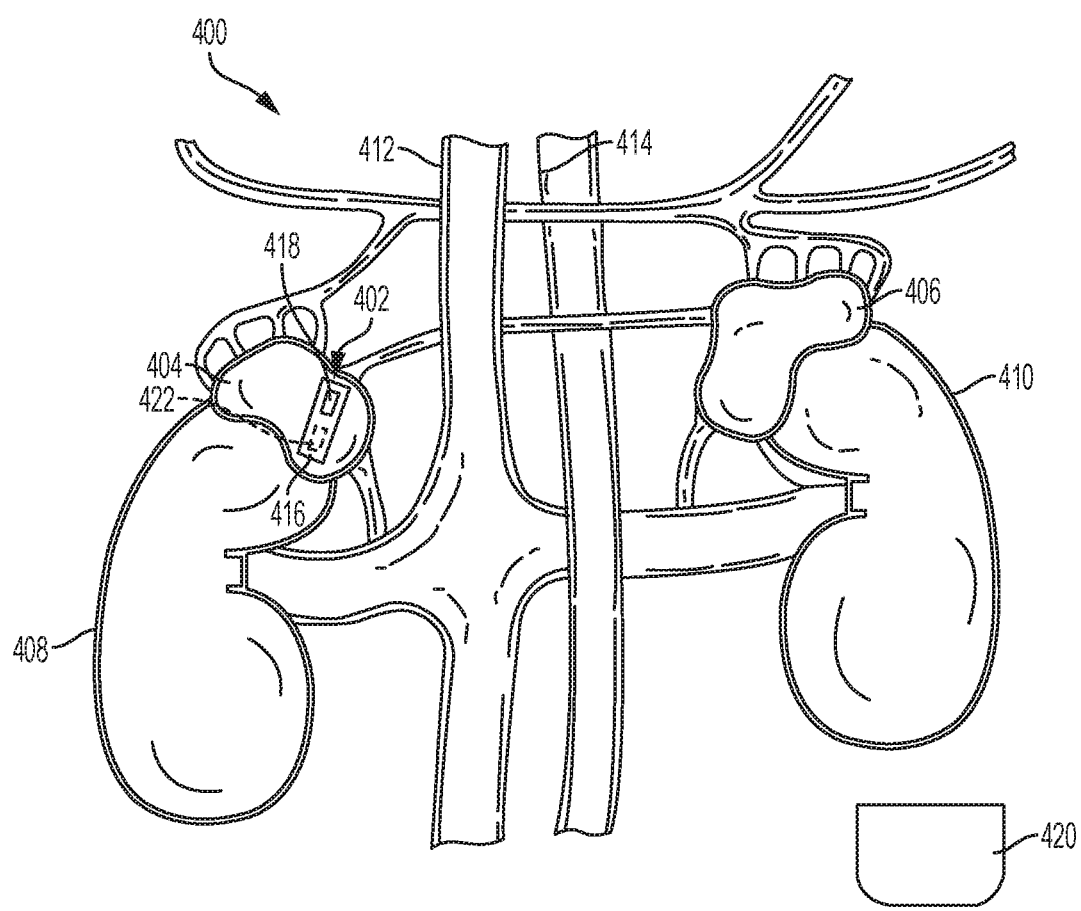
FIG. 4 is a schematic illustration of an implantable system including an implantable medical device (IMD) attached to a portion of a patient's adrenal gland in accordance with embodiments of the present disclosure.

FIG. 4 is a schematic illustration of a portion of a patient's anatomy 400 and an associated implantable system including an implantable medical device (IMD) 402 attached to a portion of a patient's adrenal gland 404, in accordance with embodiments of the present disclosure. The anatomy 400 shown in FIG. 4 includes adrenal glands 404, 406 (with Gerota's fascia), which are located above the patient's kidneys 408, 410, which are located on either side of the patient's vena cava 412 and aorta 414. The IMD 402 may include a leadless body 416 configured to engage the adrenal gland 404 (or periadrenal connective tissue), and at least one stimulation element 418 arranged with the leadless body 416. The leadless body 416 may also be attached adjacent to one or both of the adrenal glands 404, 406 (e.g., within the retroperitoneal space such as the peritoneum or submuscular region (i.e. Longissimus muscles) above the adrenal glands 404, 406). The stimulation element 418 may be configured to deliver stimulation energy to modulate production of aldosterone by the patient. In certain instances, the stimulation element 418 modulate stimulate the adrenal gland 404 and inhibit or block the release of aldosterone by the patient. More specifically, a cortex of the adrenal gland 404 may be targeted for stimulation.

In certain instances, the stimulation element 418 is configured to deliver electrical stimulation, light stimulation, sound stimulation, thermal stimulation, or magnetic stimulation to the adrenal gland 404 to modulate aldosterone levels within the patient. The stimulation element 418 may be specifically configured to deliver the intended type of stimulation energy as discussed above in detail with respect to FIG. 3. The stimulation element 418 may be configured to deliver stimulation to maintain aldosterone levels within the patient within a desired zone or range (e.g., a normal or healthy basal range as determine for the patient). The IMD 402 may communicate with a controller 420 to effect stimulation through the stimulation element 418.

As shown in FIG. 4, the IMD 402 is a wireless electrode stimulator assembly with the controller 420 configured to communicate with the IMD 402. In certain instances, the controller 420 may be co-implanted and may provide therapy and/or diagnostic data about the patient and/or the controller 420. In other instances, the controller 420 may be arranged external to the patient. The IMD 402 may include circuitry to sense and analyze the adrenal gland 404 electrical activity, and to determine if and when a pacing electrical pulse needs to be delivered and, in instances having multiple IMDs 402 (e.g., an IMD attached to adrenal gland 406), by which of the IMDs 402 the pulse should be delivered. The controller 420 may have one or more sensors (e.g., as described above with reference to FIG. 3). The sensor or sensors may also be arranged with the leadless body 416. The aldosterone levels of the patient may be sensed by the sensor and provided as feedback to the controller 420, which may alter the stimulation energy to achieve desired aldosterone levels of the patient.

The controller 420 may also analyze the signal from the sensor to calculate alteration of the stimulation energy, and alter the stimulation energy based on analysis of the signal. The data indicative of the aldosterone levels of the patient may be measured by the sensor of the controller 420 or leadless body 416, which may be a chemical sensor configured to sense chemical levels within the patient associated with the aldosterone levels, a blood pressure sensor configured to sense blood pressure levels associated with the aldosterone levels, a time of day sensor, or a sleep status sensor as discussed above in further detail with reference to FIG. 3.

In certain instances, the IMD 402 has an internal receiver that may receive communications and/or energy from the controller 420, which may include a transmitter. The controller 420 may include a pulse generator that supplies an appropriate time-varying energy (e.g., current or voltage) to the IMD 402. The IMD 402 may include a power source for storing electrical energy, and may also have a triggering mechanism to deliver stored energy to the adrenal gland via the stimulation element 418. The IMD 402 may be a passive stimulator such that stimulation energy is transmitted via the controller 420, stored with the IMD 402, and stimulated in response to a prompt from the controller 420. In other instances, the IMD 402 may be an active stimulator and provide stimulation based on control circuitry contained therein (e.g., as described in further detail in FIG. 2).

Any number of a variety of communication methods and protocols may be used, via communication links, to facilitate communication between devices in the adrenal gland therapy system discussed herein. For example, wired and/or wireless communications methods may be used. Wired communication methods may include, for example and without limitation, traditional copper-line communications such as DSL, broadband technologies such as ISDN and cable modems, and fiber optics, while wireless communications may include cellular communications, satellite communications, radio frequency (RF) communications, infrared communications, induction, conduction, acoustic communications, and/or the like.

Modulation of aldosterone, consistent with the various aspects of the present disclosure, may be non-hemodynamic. Modulation can encompass a slow rise or abrupt rise. Blunting may have abrupt compensatory rise after stimulation turned off, or may have residual blunting effects prior to plasma rise after stimulation turned off. The discovery of using electrical stimulation to modulate aldosterone levels (as opposed to use of pharmaceutical drugs) was unexpected as stimulation was not thought to interact, effect, nor disrupt the RAAS as noted above.

Aldosterone may be upregulated and downregulated depending on the stimulation applied via stimulation elements discussed herein. For sustained reduction in aldosterone levels, for example, stimulation may be applied continuously at a frequency between approximately 2 Hz and approximately 20 kHz or between approximately 20 Hz and approximately 4000 Hz with or without a duty cycle including brief on/off periods (e.g., 30 seconds ON, 30 seconds OFF repeated for a duration of time such, then completely off for a duration of time), continuously applied for an extended period of time (e.g., greater than 1 hour with or without brief off periods). A quick compensatory rise in aldosterone may be seen when stimulation is turn off for example, after a longer stimulation time period followed by a shorter period of no stimulation (e.g., 90 min ON/30 min OFF). This duty cycle may be used as a means of titrating therapy (e.g., lesser magnitude of reduction in Aldosterone vs. 100% stimulation) or for preserved battery life. An example to increase Aldosterone may be to apply stimulation for a brief period of time (e.g., 1 to 15 minutes) followed by a period of no stimulation, where a rebound effect is expected followed by a period of elevated aldosterone levels. A rise from baseline may also result. Using sensors that provide an indication of aldosterone, such as those discussed herein with reference to FIG. 3, the therapy may be a 'closed loop therapy' to automatically or semi-automatically titrate and deliver therapy in response to the sensed parameters.

Various modifications and additions can be made to the exemplary embodiments discussed without departing from the scope of the present disclosure. For example, while the embodiments described above refer to particular features, the scope of the subject matter disclosed herein also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An apparatus for delivering therapy to an adrenal gland of a patient, the apparatus comprising:
 a housing sized and configured to attach between a capsule surrounding the adrenal gland and remaining portions of the adrenal gland;
 a plurality of stimulation elements arranged with the housing configured to deliver stimulation energy through at least one of the plurality of stimulation elements to modulate production of aldosterone by the patient; and
 a controller configured to instruct alteration of the stimulation energy on a duty cycle based on a metabolization time of aldosterone within the patient in response to feedback based on symptoms of the patient to maintain aldosterone levels within the patient to a calibrated target level or within normal basal levels of the patient.

2. The apparatus of claim 1, wherein the plurality of stimulation elements are configured to stimulate the adrenal gland and inhibit or block the release of aldosterone by the patient.

3. The apparatus of claim 1, wherein the housing is a leadless housing configured to engage the portion of the adrenal gland.

4. The apparatus of claim 1, wherein the housing is a lead body configured to engage the portion of the adrenal gland.

5. The apparatus of claim 1, wherein the plurality of stimulation elements are configured to deliver at least one of electrical stimulation, light stimulation, sound stimulation, thermal stimulation, and magnetic stimulation to the adrenal gland to modulate the aldosterone levels within the patient.

6. The apparatus of claim 1, wherein the plurality of stimulation elements are configured to deliver stimulation to maintain the aldosterone levels within the patient within normal basal levels.

7. The apparatus of claim 1, wherein the plurality of stimulation elements are configured to deliver stimulation energy at a frequency between 2 Hz and 20 kHz.

8. The apparatus of claim 1, wherein the plurality of stimulation elements are configured to deliver stimulation energy to a cortex or outer layer of the adrenal gland of the patient.

9. The apparatus of claim 8, wherein the delivery of stimulation energy modulates the renin-angiotensin-aldosterone system (RAAS) within the patient.

10. The apparatus of claim 9, wherein the delivery of stimulation energy interrupts the renin-angiotensin-aldosterone system (RAAS) thereby lowering production of aldosterone by the patient.

11. The apparatus of claim 1, wherein the delivery of stimulation energy lessens aldosterone plasma levels in the patient to treat at least one of heart failure, chronic kidney disease, and cardiorenal syndrome.

12. An apparatus for delivering therapy to an adrenal gland of a patient, the apparatus comprising:
  a housing sized and configured to attach between a capsule surrounding the adrenal gland and remaining portions of the adrenal gland;
  a plurality of stimulation elements arranged with the housing configured to deliver stimulation energy through at least one of the plurality of stimulation elements to modulate aldosterone levels within the patient;
  a sensor configured to measure the aldosterone levels within the patient; and
  a controller configured to instruct alteration of the stimulation energy on a duty cycle based on a metabolization time of aldosterone within the patient in response to feedback based on the aldosterone levels measured by the sensor to maintain the aldosterone levels within the patient to a calibrated target level or within normal basal levels of the patient.

13. The apparatus of claim 12, wherein the sensor is configured to alter the stimulation energy delivered through the at least one of the plurality of stimulation elements to maintain the aldosterone levels within the patient within normal basal levels.

14. The apparatus of claim 12, wherein the sensor is arranged with the housing.

15. The apparatus of claim 12, wherein the housing comprises a communications component configured to communicate wireless signals, and the sensor is configured to measure the aldosterone levels within the patient and communicate feedback to the communication component via wireless signals to alter the stimulation energy delivered through the at least one of the plurality of stimulation elements to maintain the aldosterone levels within the patient within the normal basal levels of the patient.

16. The apparatus of claim 12, wherein the sensor is at least one of a chemical sensor configured to sense chemical levels within the patient associated with the aldosterone levels, a blood pressure sensor configured to sense blood pressure levels associated with the aldosterone levels, a time of day sensor configured to sense blood pressure levels associated with the aldosterone levels, and a sleep status sensor configured to sense blood pressure levels associated with the aldosterone levels.

17. A method of delivering therapy to an adrenal gland of a patient, the method comprising:
  delivering a housing sized and configured to implant between a portion of the adrenal gland of the patient and a capsule surrounding the adrenal gland, the housing including a plurality of stimulation elements arranged with the housing;
  delivering stimulation energy through at least one of a plurality of electrodes leadless implantable medical energy on a duty cycle based on a metabolization time of aldosterone within the patient to modulate aldosterone levels within the patient; and
  instructing alteration of the stimulation energy in response to feedback based on symptoms of the patient to maintain aldosterone levels within the patient to a calibrated target level or within normal basal levels of the patient.

18. The method of claim 17, further comprising using a sensor to measure the aldosterone levels within the patient and altering the stimulation energy delivered through the at least one of the plurality of stimulation elements based on measured aldosterone levels.

* * * * *